United States Patent [19]
Shelton et al.

[11] Patent Number: 5,441,525
[45] Date of Patent: Aug. 15, 1995

[54] PACEMAKER WITH VASOVAGAL SYNCOPE DETECTION

[75] Inventors: Michael B. Shelton, Minneapolis; Kenneth M. Riff, Plymouth; Michael F. Hess, Minneapolis, all of Minn.

[73] Assignee: Medtronic, Inc., Minneapolis, Minn.

[21] Appl. No.: 246,903

[22] Filed: May 20, 1994

[51] Int. Cl.$^6$ ............................................. A61N 1/36
[52] U.S. Cl. ............................................ 607/23; 607/6; 128/706
[58] Field of Search ............... 607/6, 9, 18, 23, 24; 128/706

[56] References Cited

U.S. PATENT DOCUMENTS 4,556,063 12/1985 Thompson .
4,880,005 11/1989 Pless .
5,127,404 7/1992 Wyborny .

Primary Examiner—William E. Kamm
Assistant Examiner—Scott M. Getzow
Attorney, Agent, or Firm—Harold R. Patton

[57] ABSTRACT

A rate-responsive cardiac pacemaker implements a novel scheme which detects incipient vasovagal syncope (or other episodes caused by a vasodepressive or cardioinhibitory disorder) when a) the heart rate drops below a programmable minimum size, and b) the rate after said drop is below a programmable maximum drop ending rate. The pacemaker implements a stability and intervention procedure upon the detection of an episode, in which it ignores transient drops in rate, and paces at a predetermined high rate if the drops are stable. The pacemaker then gradually reduces the pacing rate over a predetermined time to the pre-episodic level. A sleep disable feature disables the vasovagal syncope detection and therapy features during the patient's sleeping hours to reduce or eliminate false positive responses.

16 Claims, 4 Drawing Sheets

PACEMAKER WITH VASOVAGAL SYNCOPE DETECTION

FIELD OF THE INVENTION

The present invention generally relates to artificial cardiac pacemakers, and the treatment of patients who have vasodepressor or cardioinhibitory disorders. More specifically, the present invention relates to the treatment of patients who experience vasovagal syncope episodes.

BACKGROUND OF THE INVENTION

Generally speaking, a cardiac pacemaker is an electrical device used to supplant some or all of an abnormal heart's natural pacing function, by delivering appropriately timed electrical stimulation signals designed to cause the myocardium of the heart to contract or "beat".

Vasovagal syncope is a condition marked by a sudden drop in blood pressure resulting in fainting. It is not only unpleasant for a patient, but potentially dangerous, as fainting may lead to injuries from falls.

Therapy to counteract a vasovagal syncope episode is possible through use of an implanted cardiac pacemaker. What is needed, then, is a reliable means of detecting the onset of a vasovagal syncope episode, so that the pacemaker can deliver the therapy when it is needed.

SUMMARY OF THE INVENTION

In view of the foregoing, it is a first object of the present invention to provide a cardiac pacemaker capable of detecting episodes reflective of vasodepressor or cardioinhibitory disorders.

It is a second object of the present invention to satisfy the first object specifically with respect to incipient vasovagal syncope.

It is a third object of the present invention to satisfy the first and second objects with an emphasis on preventing "false positives."

In order to satisfy the above objects and others, the present invention provides a cardiac pacemaker for detecting the onset of a cardioinhibitory episode at least including:

heart rate drop determination means for determining the size of a drop in heart rate;

minimum rate drop storage means for storing a programmable minimum rate drop;

minimum rate storage means for storing a programmable maximum drop ending rate;

comparator means coupled to the heart rate drop determination means, the minimum rate drop storage means, and the minimum rate storage means for comparing the size of the drop in rate to the minimum rate drop, and for comparing an ending rate to the maximum drop ending rate, the ending rate being defined as the heart rate at the time the rate drop is determined; and cardioinhibitory indication means coupled to the comparator means for indicating the occurrence of a cardioinhibitory episode when the rate drop exceeds the minimum rate drop and the ending rate is below the maximum drop ending rate.

The present invention further provides a cardioinhibitory detection method adapted for use in a cardiac pacemaker for detecting the onset of cardioinhibitory episode at least including the steps of:

determining the size of a drop in heart rate;
storing a programmable minimum rate drop;
storing a programmable maximum drop ending rate; and comparing the size of the drop in rate to the minimum rate drop, and for comparing an ending rate to the maximum drop ending rate, the ending rate being defined as the heart rate at the time the rate drop is determined; and indicating the occurrence of a cardioinhibitory episode when the rate drop exceeds the minimum rate drop and the ending rate is below the maximum drop ending rate.

The details of the present invention will be revealed in the following description, with reference to the attached drawing.

BRIEF DESCRIPTION OF THE DRAWING

The various figures of the drawing are briefly described as follows.

DETAILED DESCRIPTION OF THE INVENTION

Part I. Elementary Description

Figure 1:
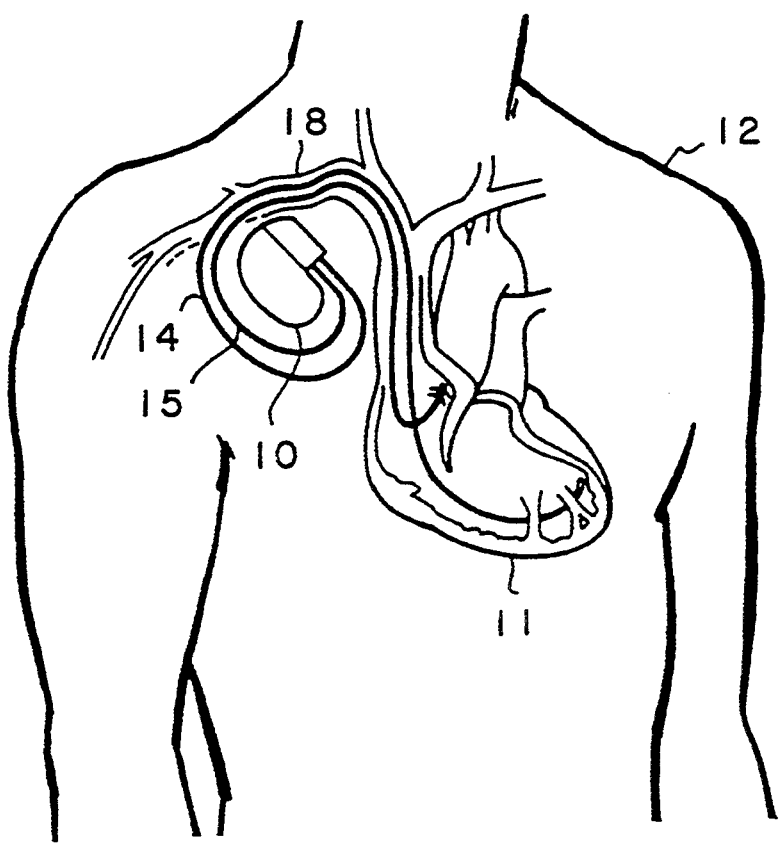
FIG. 1 is a diagram showing the heart of a patient electrically connected to the pacemaker in FIG. 2.

FIG. 1 generally shows a pacemaker 10 implanted in a patient 12. The pacemaker leads 14 and 15 electrically couple the pacemaker 10 to the patient's heart 11 via a suitable vein 18. The leads act to both sense polarizations in the heart, and to deliver pacing stimuli the heart.

Part II. General Description of the Pacemaker Device

Figure 2:
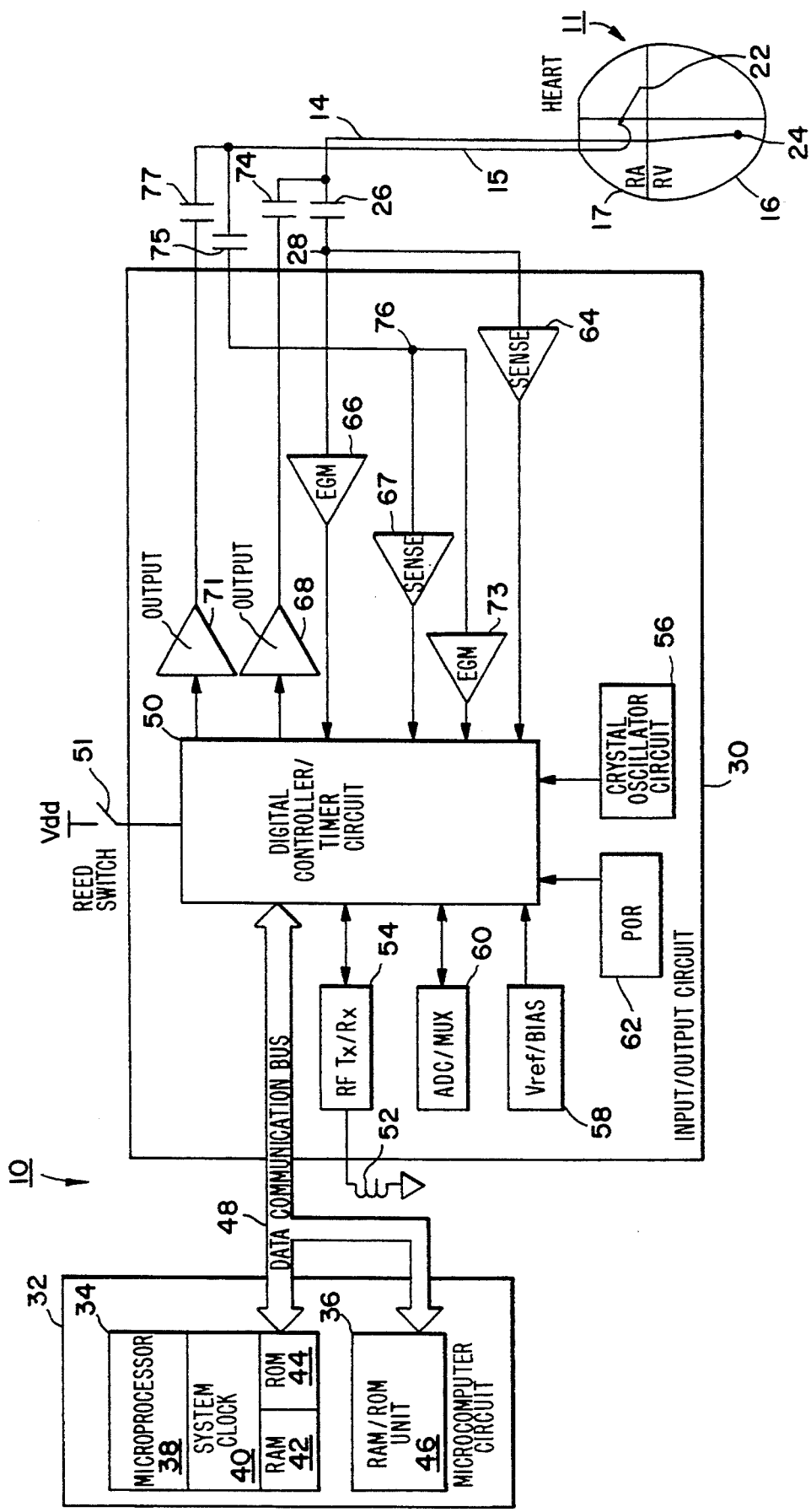
FIG. 2 is a schematic block diagram of a multi-sensor, rate-responsive, dual chamber implantable pulse generator (IPG) capable of subsuming the present invention.

FIG. 2 is a block circuit diagram illustrating a multi-programmable, implantable, dual-chamber, bradycardia pacemaker 10 capable of carrying out the present invention. Although the present invention is described in conjunction with a microprocessor-based architecture, it will be understood that it could be implemented in other technology such as digital logic-based, custom integrated circuit (IC) architecture, if desired. It will also be understood that the present invention may be implemented in cardioverters, defibrillators and the like.

Lead 14 includes an intracardiac electrode 24 located near its distal end and positioned within the right ventricle 16. Electrode 24 is coupled by a lead conductor 14 through an input capacitor 26 to the node 28, and to the input/output terminals of an input/output circuit 30.

Similarly, the lead 15 has a distally located intracardiac electrode positioned within the right atrium 17. Electrode 22 is coupled by a lead conductor 15 through an input capacitor 75 to a node 76, and to the input/output terminals of the input/output circuit 30.

Input/Output Circuit 30 contains the operating input and output analog circuits for digital controlling and timing circuits necessary for the detection of electrical signals derived from the heart, such as the cardiac electrogram, output from sensors (not shown) connected to the leads 14 and 15, as well as for the application of stimulating pulses to the heart to control its rate as a function thereof under the control of software-implemented algorithms in a Microcomputer Circuit 32.

Microcomputer Circuit 32 comprises an On-Board Circuit 34 and an Off-Board Circuit 36. On-Board Circuit 34 includes a microprocessor 38, a system clock 40, and on-board RAM 42 and ROM 44. Off-Board Circuit 36 includes an off-board RAM/ROM Unit 46. Microcomputer Circuit 32 is coupled by Data Communication Bus 48 to a Digital Controller/Timer Circuit 50. Microcomputer Circuit 32 may be fabricated of custom IC devices augmented by standard RAM/ROM components.

It will be understood by those skilled in the art that the electrical components represented in FIG. 2 are powered by an appropriate implantable-grade battery power source (not shown).

An antenna 52 is connected to Input/Output Circuit 30 for purposes of uplink/downlink telemetry through a radio frequency (RF) Transmitter/Receiver Circuit (RF TX/RX) 54. Telemetering both analog and digital data between antenna 52 and an external device, such as an external programmer (not shown), is accomplished in the preferred embodiment by means of all data first being digitally encoded and then pulse position modulated on a damped RF carrier, as substantially described in U.S. Pat. No. 5,127,404, issued on Jul. 7, 1992, entitled "Telemetry Format for Implantable Medical Device", which is held by the same assignee as the present invention and which is incorporated herein by reference. A reed switch 51 is connected to Input/Output Circuit 30 to enable patient follow-up via disabling the sense amplifier 146 and enabling telemetry and programming functions, as is known in the art.

A Crystal Oscillator Circuit 56, typically a 32,768 Hz crystal-controlled oscillator, provides main timing clock signals to Digital Controller/Timer Circuit 50. A Vref/Bias Circuit 58 generates a stable voltage reference and bias currents for the analog circuits of Input/Output Circuit 30. An ADC/Multiplexer Circuit (ADC/MUX) 60 digitizes analog signals and voltages to provide telemetry and a replacement time-indicating or end-of-life function (EOL). A Power-on-Reset Circuit (POR) 62 functions to initialize the pacemaker 10 with programmed values during power-up, and reset the program values to default states upon the detection of a low battery condition or transiently in the presence of certain undesirable conditions such as unacceptably high electromagnetic interference (EMI), for example.

The operating commands for controlling the timing of the pacemaker depicted in FIG. 2 are coupled by bus 48 to Digital Controller/Timer Circuit 50 wherein digital timers set the overall escape interval of the pacemaker, as well as various refractory, blanking and other timing windows for controlling the operation of the peripheral components within Input/Output Circuit 50.

Digital Controller/Timer Circuit 50 is coupled to sense amplifiers (SENSE) 64 and 67, and to electrogram (EGM) amplifiers 66 and 73 for receiving amplified and processed signals picked up from electrode 24 through lead 14 and capacitor 26, and for receiving amplified and processed signals picked up from electrode 22 through lead 15 and capacitor 75, representative of the electrical activity of the patient's ventricle 16 and atrium 17, respectively. Similarly, SENSE amplifiers 64 and 67 produce sense event signals for re-setting the escape interval timer within Circuit 50. The electrogram signal developed by EGM amplifier 66 is used in those occasions when the implanted device is being interrogated by the external programmer/transceiver (not shown) in order to transmit by uplink telemetry a representation of the analog electrogram of the patient's electrical heart activity as described in U.S. Pat. No. 4,556,063, issued to Thompson et al., entitled "Telemetry System for a Medical Device", which is held by the same assignee as the present invention, and which is incorporated herein by reference.

Output pulse generators 68 and 71 provide the pacing stimuli to the patient's heart 11 through output capacitors 74 and 77 and leads 14 and 15 in response to paced trigger signals developed by Digital Controller/Timer Circuit 50 each time the escape interval times out, or an externally transmitted pacing command has been received, or in response to other stored commands as is well known in the pacing art.

In a preferred embodiment of the present invention, pacemaker 10 is capable of operating in various non-rate-responsive modes which include DDD, DDI, VVI, VOO and VVT, as well as corresponding rate-responsive modes of DDDR, DDIR, VVIR, VOOR and VVTR. Further, pacemaker 10 can be programmably configured to operate such that it varies its rate only in response to one selected sensor output, or in response to both sensor outputs, if desired.

Part III. Vasovagal Syncope Detection Feature

Details of the vasovagal syncope detection feature of the present invention follow below, with reference to the graph 300 in FIG. 3. It should be understood that the present invention is not limited to the detection of vasovagal syncope, and it can be used to detect episodes reflective of other vasodepressor or cardioinhibitory disorders such as carotid sinus syndrome.

In the graph, a lower rate 302 is shown—a rate below which the heart will not be allowed to fall (also known as the escape rate in this instance). The detection algorithm contains three parameters used to determine the presence, vel non., of a vasovagal syncope episode.

The detection algorithm is triggered when the heart rate (atrial or ventricular) of the current cycle ($R_N$) is less than the heart rate of a predetermined previous cycle $R_{N-M}$, where M is an integer. A programmable quantity, M equals two in the preferred embodiment, so that the reference cycle is the one twice removed ($R_{N-2}$). It should be understood that M may be a number other than 2. For example, M equals 5 in an alternate embodiment so that the heart rate compared is five cycles removed.

The drop (304 in FIG. 3) is compared to a programmable minimum rate drop, which is 20 beats per minute (BPM) in the preferred embodiment. If the actual rate drop is less than or equal to the minimum rate drop, the algorithm halts, and the control of the pacemaker 10 is returned to the main program.

Figure 3:
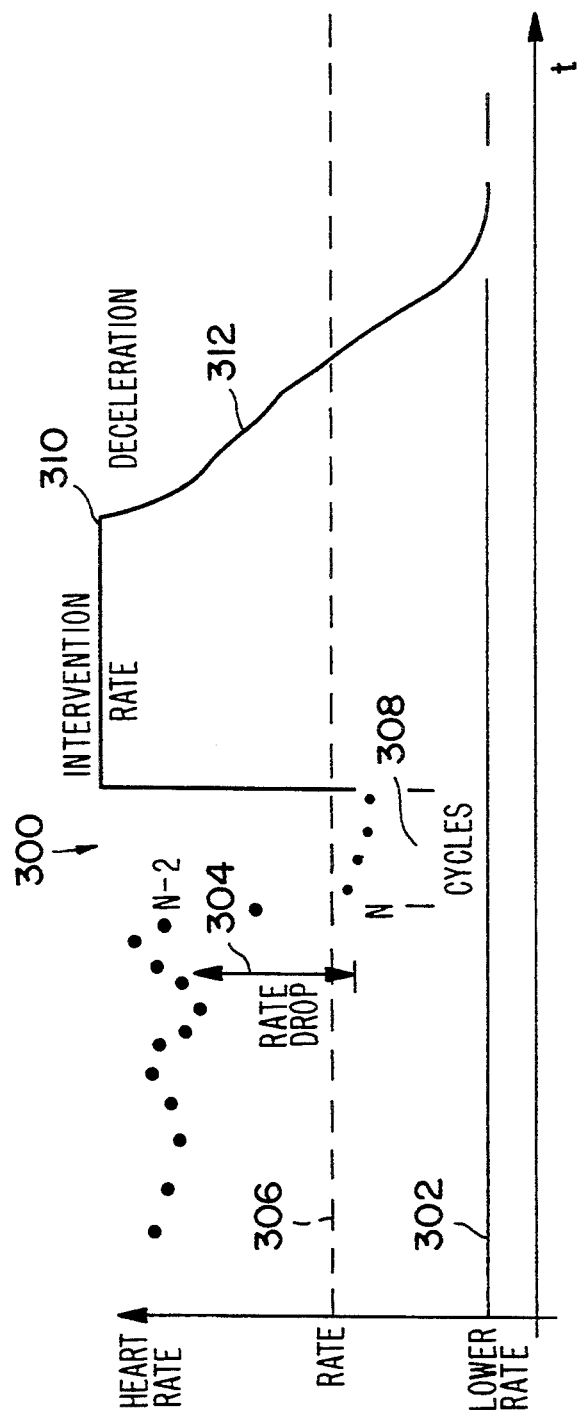
FIG. 3 is a graph of heart rate versus time illustrating the vasovagal syncope detection method of the present invention.

If the actual rate drop (also known as the drop ending rate) exceeds the minimum rate drop, the heart rate of the current cycle is then compared to a programmable maximum drop ending rate (306 in FIG. 3). The maximum drop ending rate is the highest heart rate that would not be considered severely bradycardic. If the drop ending rate is greater than or equal to the maximum drop ending rate, the algorithm continues searching for the above-mentioned trigger criteria.

If the drop ending rate is below the maximum drop ending rate, the algorithm proceeds to count the number of consecutive cycles (308 in FIG. 3) that both the rate drop has been greater than the minimum rate drop and the drop ending rate has been below the maximum drop ending rate. This number is compared to a programmable minimum consecutive cycle number, which is 2 in the preferred embodiment. If the number of consecutive cycles is less than the minimum consecutive cycle number, the control of the pacemaker 10 is returned to the main program. If the number of consecutive cycles is greater than or equal to the minimum consecutive cycle number, the occurrence of a vasovagal syncope episode is indicated, causing the pacemaker 10 to deliver a predetermined vasovagal syncope prevention or elimination therapy.

Segments 310 and 312 generally illustrate the application of pacemaker therapy used to prevent or eliminate a vasovagal syncope episode upon its detection.

Part IV. Sleep Disabling Feature

To further prevent false positives, the present invention disables the detection feature of the present invention while the patient is presumed to be asleep. Otherwise, a low heart rate normally associated with sleeping might be erroneously associated with bradycardia which accompanies a vasovagal syncope episode. Such a malfunction would unnecessarily lead to disturbing the patient's sleep by raising his or her heart rate to a high intervention rate.

This feature is implemented in the present invention with the use of a diurnal clock (not shown) in the microcomputer circuit 32 which causes the microcomputer circuit 32 to disable the detection feature during presumed sleeping hours. The sleeping hours of the diurnal cycle are programmed prior to implant to suit the individual patient's lifestyle.

Part V. Rate Drop Size Determination (Alternate Embodiment)

Figure 4:
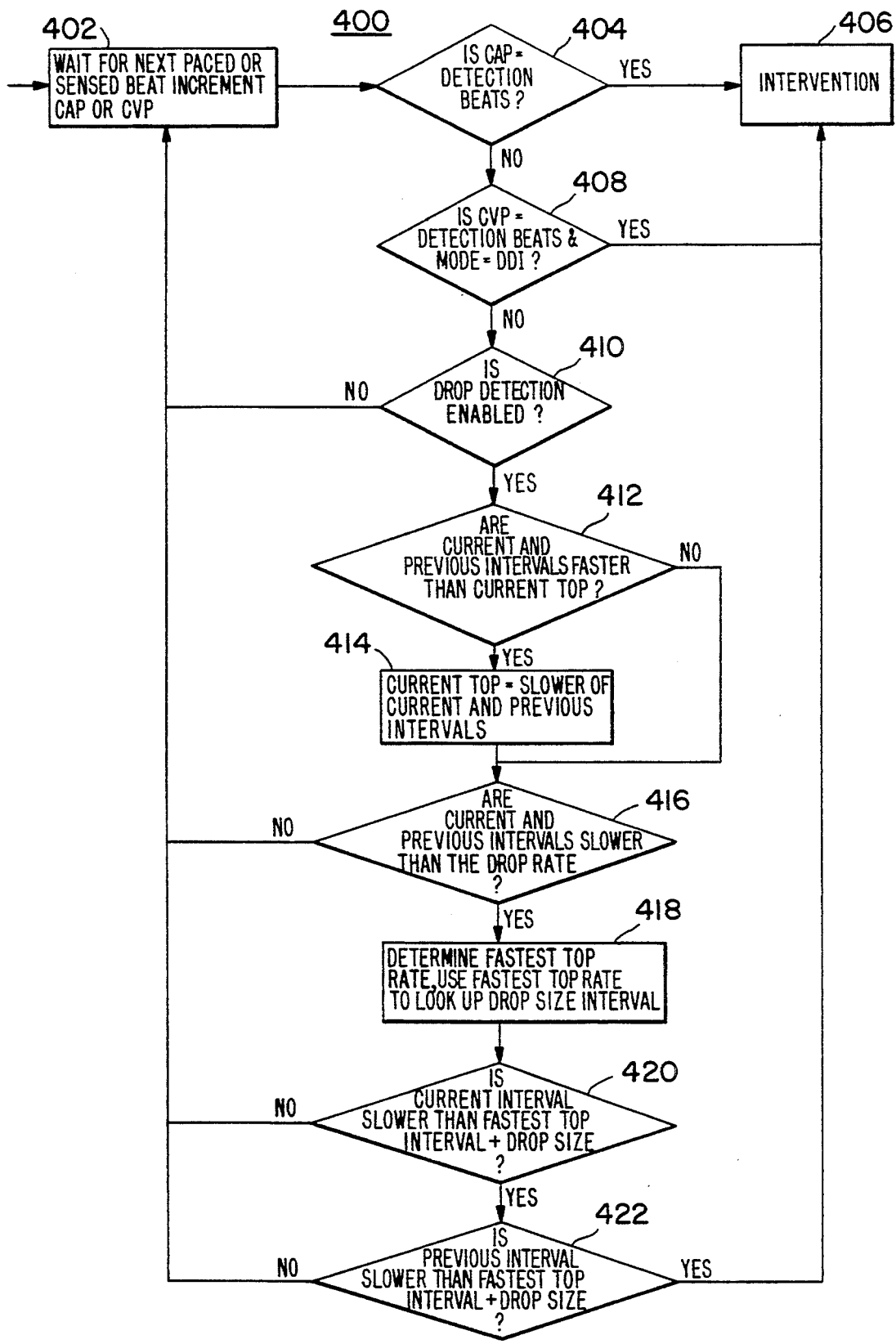
FIG. 4 is a flowchart detailing an alternate embodiment for the rate drop size determination of the present invention.

FIG. 4 is a flowchart describing a program 400 for implementing an alternate embodiment for computing the rate drop size 304. To summarize the method, the pacemaker 10 compares the current rate to the highest of 5 stored rates sampled over the previous 2.5 minutes (each of the 5 samples is the highest rate of all the beats occurring in its corresponding 30 second interval) to determine the rate drop.

During the operation of the program 400 two counters (not shown) keep track of the number of consecutive atrial paces (CAP) and consecutive ventricular paces (CVP) meeting the criteria for detection of a WS episode. At Step 402 CAP is incremented whenever an atrial pace occurs, and reset to zero whenever an atrial sense occurs. Likewise, CVP is incremented whenever a ventricular pace occurs, and reset to zero whenever a ventricular sense occurs. At Step 404 if CAP equals the number of consecutive beats required to indicate detection, the program 400 then advances to Step 406 where the pacemaker 10 can begin interventional therapy. If CAP does not equal the required number of detection beats, the program 400 advances to Step 408.

At Step 408, if the current pacing mode is DDI and CVP equals the required number of detection beats, intervention (detection of a VVS episode) is indicated (Step 406). If these conditions are not met, the program advances to Step 410. If the drop detection feature of the pacemaker 10 is enabled, the program continues to Step 412; otherwise, the program returns to Step 402. The "Current Top" at Step 412 refers to the lowest rate observed during the previous 2.5 minutes. Conversely, the current top also refers to the largest interval between beats observed during the previous 2.5 minutes.

If the current and previous intervals between beats are lower than the Current Top, the program advances to Step 414; otherwise the program jumps to Step 416. A new Current Top is stored at Step 414. At Step 416, the pacemaker determines whether the current and previous intervals are slower than the interval corresponding to the Drop Rate. If these intervals are not slower than the Drop Rate interval, the program returns to Step 402. If the intervals are slower the Drop Rate interval, the program advances to Step 418 to begin examining the size of the rate drop.

At Step 418 the program determines the Drop Size interval from a look-up table based upon the fastest stored Top Rate and the programmed rate drop. If the current interval is slower than the fastest Top interval plus the Drop Size interval (Step 420), the program advances to Step 422. At Step 422, if the previous interval was also slower than the fastest Top interval plus the Drop Size interval, detection of a VVS episode is indicated by returning the program to Step 406. Steps 420 and 422 insure that at least two consecutive beats meet the conditions for VVS before indicating detection. This will prevent frequent, unnecessary triggering of intervention therapy where the presence of the identified characteristics is only transient in nature.

Variations and modifications to the present invention are possible given the above disclosure. However, such variations and modifications are intended to be within the scope of the invention claimed by this letters patent. For example, the maximum drop need not be 20 BPM, but may be any other suitable number, as may be established by one (either at manufacture or just prior to implantation, or after implantation using remote programming means) skilled in the art. Similarly, the maximum drop ending rate is not limited to 65 BPM. And, the minimum consecutive cycle number may be any suitable whole number.

We claim:

1. A cardiac pacemaker for detecting the onset of a cardioinhibitory episode comprising:
   heart rate drop determination means for determining the size of a drop in heart rate;
   minimum rate drop storage means for storing a programmable minimum rate drop;
   minimum rate storage means for storing a programmable maximum drop ending rate;
   comparator means coupled to said heart rate drop determination means, said minimum rate drop storage means, and said minimum rate storage means for comparing the size of said drop in rate to said minimum rate drop, and for comparing an ending rate to said maximum drop ending rate, said ending rate being defined as the heart rate at the time said rate drop is determined; and
   cardioinhibitory indication means coupled to said comparator means for indicating the occurrence of a cardioinhibitory episode when said rate drop exceeds said minimum rate drop and said ending rate is below said maximum drop ending rate.

2. The cardiac pacemaker in claim 1 wherein said cardioinhibitory indication means further comprises consecutive cycle counter means for enabling said cardioinhibitory indication means to indicate the occurrence of a cardioinhibitory episode only after counting a predetermined number of consecutive cardiac cycles in which said rate drop exceeds said minimum rate drop and said ending rate is below said maximum drop ending rate.

3. The cardiac pacemaker in claim 1 further comprising:
sleep period determination means for determining at least one sleep period; and
disable means coupled to said cardioinhibitory indication means for disabling said cardioinhibitory indication means during a determined sleep period.

4. The cardiac pacemaker in claim 3 wherein said sleep period determination means further comprises clock means for keeping track of a patient's diurnal cycle.

5. A cardioinhibitory detection method adapted for use in a cardiac pacemaker for detecting the onset of cardioinhibitory episode comprising the steps of:
determining the size of a drop in heart rate;
storing a programmable minimum rate drop;
storing a programmable maximum drop ending rate; and
comparing the size of said drop in rate to said minimum rate drop, and for comparing an ending rate to said maximum drop ending rate, said ending rate being defined as the heart rate at the time said rate drop is determined; and
indicating the occurrence of a cardioinhibitory episode when said rate drop exceeds said minimum rate drop and said ending rate is below said maximum drop ending rate.

6. The cardioinhibitory detection method in claim 5 further comprising the steps of:
counting the number of consecutive cardiac cycles in which said rate drop exceeds said minimum rate drop and said ending rate is below said maximum drop ending rate; and
enabling the indication of the occurrence of a cardioinhibitory episode only when said number of consecutive cycles at least equals a predetermined number.

7. The cardiac pacing method in claim 5 further comprising the steps of:
determining at least one sleep period; and
disabling said cardioinhibitory indication step during a determined sleep period.

8. The cardiac pacing method in claim 7 wherein the sleep period determining step further comprises keeping track of a patient's diurnal cycle.

9. A cardiac pacemaker for detecting the onset of a vasovagal syncope episode comprising:
heart rate drop determination means for determining the size of a drop in heart rate;
minimum rate drop storage means for storing a programmable minimum rate drop;
minimum rate storage means for storing a programmable maximum drop ending rate;
comparator means coupled to said heart rate drop determination means, said minimum rate drop storage means, and said minimum rate storage means for comparing the size of said drop in rate to said minimum rate drop, and for comparing an ending rate to said maximum drop ending rate, said ending rate being defined as the heart rate at the time said rate drop is determined; and
vasovagal syncope indication means coupled to said comparator means for indicating the occurrence of a vasovagal syncope episode when said rate drop exceeds said minimum rate drop and said ending rate is below said maximum drop ending rate.

10. The cardiac pacemaker in claim 9 wherein said vasovagal syncope indication means further comprises consecutive cycle counter means for enabling said vasovagal syncope indication means to indicate the occurrence of a vasovagal syncope episode only after counting a predetermined number of consecutive cardiac cycles in which said rate drop exceeds said minimum rate drop and said ending rate is below said maximum drop ending rate.

11. The cardiac pacemaker in claim 9 further comprising:
sleep period determination means for determining at least one sleep period; and
disable means coupled to said vasovagal syncope indication means for disabling said vasovagal syncope indication means during a determined sleep period.

12. The cardiac pacemaker in claim 11 wherein said sleep period determination means further comprises clock means for keeping track of a patient's diurnal cycle.

13. A vasovagal syncope detection method adapted for use in a cardiac pacemaker for detecting the onset of vasovagal syncope episode comprising the steps of:
determining the size of a drop in heart rate;
storing a programmable minimum rate drop;
storing a programmable maximum drop ending rate; and
comparing the size of said drop in rate to said minimum rate drop, and for comparing an ending rate to said maximum drop ending rate, said ending rate being defined as the heart rate at the time said rate drop is determined; and
indicating the occurrence of a vasovagal syncope episode when said rate drop exceeds said minimum rate drop and said ending rate is below said maximum drop ending rate.

14. The vasovagal syncope detection method in claim 13 further comprising the steps of:
counting the number of consecutive cardiac cycles in which said rate drop exceeds said minimum rate drop and said ending rate is below said maximum drop ending rate; and
enabling the indication of the occurrence of a vasovagal syncope episode only when said number of consecutive cycles at least equals a predetermined number.

15. The cardiac pacing method in claim 13 further comprising the steps of:
determining at least one sleep period; and
disabling said vasovagal syncope indication step during a determined sleep period.

16. The cardiac pacing method in claim 15 wherein the sleep period determining step further comprises keeping track of a patient's diurnal cycle.

* * * * *